US00PP29854P2

(12) United States Plant Patent
van den Hoogen

(10) Patent No.: US PP29,854 P2
(45) Date of Patent: Nov. 20, 2018

(54) ***VERONICA* PLANT NAMED 'ALLVBRIDE'**

(50) Latin Name: *Veronica longifolia*
Varietal Denomination: Allvbride

(71) Applicant: Wilhelmus T. J. van den Hoogen, Cuijk (NL)

(72) Inventor: Wilhelmus T. J. van den Hoogen, Cuijk (NL)

(73) Assignee: Allplants Holding B.V., Cuijk (NL)

( * ) Notice: Subject to any disclaimer, the term of this patent is extended or adjusted under 35 U.S.C. 154(b) by 0 days.

(21) Appl. No.: 15/732,569

(22) Filed: Nov. 29, 2017

(51) Int. Cl.
*A01H 5/02* (2018.01)

(52) U.S. Cl.
USPC ..... Plt./251
CPC ..... *A01H 5/02* (2013.01)

(58) Field of Classification Search
USPC ..... Plt./251
CPC ..... A01H 5/02
See application file for complete search history.

(56) References Cited

FOREIGN PATENT DOCUMENTS

QZ PBR 20171755 10/2017

*Primary Examiner* — Kent L Bell
(74) *Attorney, Agent, or Firm* — C. A. Whealy

(57) ABSTRACT

A new and distinct cultivar of *Veronica* plant named 'Allvbride', characterized by its upright and somewhat outwardly spreading plant habit; relatively small dark green-colored leaves; freely flowering habit; dense inflorescences with numerous white-colored flowers; long flowering period; and suitability as a garden plant.

2 Drawing Sheets

Botanical designation: *Veronica longifolia.*
Cultivar denomination: 'ALLVBRIDE'.

BACKGROUND OF THE INVENTION

The present invention relates to a new and distinct cultivar of *Veronica* plant, botanically known as *Veronica longifolia* and hereinafter referred to by the name 'Allvbride'.

The new *Veronica* plant is a product of a planned breeding program conducted by the Inventor in Cuijk, The Netherlands. The objective of the breeding program is to create new attractive *Veronica* plants that are suitable as garden plants.

The new *Veronica* plant originated from an open-pollination in September, 2014 of a proprietary selection of *Veronica longifolia* identified as code number 1-2013-74-11, not patented, as the female, or seed, parent with an unknown selection of *Veronica longifolia* as the male, or pollen, parent. The new *Veronica* plant was discovered and selected by the Inventor as a single flowering plant from within the progeny of the stated open-pollination in a controlled nursery environment in Cuijk, The Netherlands in July, 2015.

Asexual reproduction of the new *Veronica* plant by terminal cuttings in a controlled environment in Cuijk, The Netherlands, since September, 2015 has shown that the unique features of this new *Veronica* plant are stable and reproduced true to type in successive generations.

SUMMARY OF THE INVENTION

Plants of the new *Veronica* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Allvbride'. These characteristics in combination distinguish 'Allvbride' as a new and distinct *Veronica* plant:

1. Upright and somewhat outwardly spreading plant habit.
2. Relatively small dark green-colored leaves.
3. Freely flowering habit.
4. Dense inflorescences with numerous white-colored flowers.
5. Long flowering period.
6. Suitable as a garden plant.

Plants of the new *Veronica* differ primarily from plants of the female parent selection in the following characteristics:

1. Plants of the new *Veronica* are more freely branching than plants of the female parent selection.
2. Plants of the new *Veronica* have smaller and slightly darker green-colored leaves than plants of the female parent selection.
3. Plants of the new *Veronica* are more freely flowering than plants of the female parent selection.

Plants of the new *Veronica* can be compared to plants of *Veronica longifolia* 'Alllady', disclosed in U.S. Plant Pat. No. 23,271. In side-by-side comparisons, plants of the new *Veronica* differ primarily from plants of 'Alllady' in the following characteristics:

1. Lateral branches of the new *Veronica* develop lower on the plant than lateral branches of plants of 'Alllady'.
2. Leaves of plants of the new *Veronica* are smaller than leaves of plants of 'Alllady'.
3. Inflorescences of plants of the new *Veronica* are longer than inflorescences of 'Alllady'.

BRIEF DESCRIPTION OF THE PHOTOGRAPHS

The accompanying colored photographs illustrate the overall appearance of the *Veronica* plant showing the colors as true as it is reasonably possible to obtain in colored reproductions of this type. Colors in the photographs may differ slightly from the color values cited in the detailed botanical description which accurately describe the actual colors of the new *Veronica* plant.

The photograph on the first sheet comprises a side perspective view of a typical flowering plant of 'Allvbride' grown in a container.

The photograph at the top of the second sheet is a close-up view of the upper surface of a typical leaf of 'Allvbride'.

The photograph at the bottom of the second sheet is a close-up view of typical inflorescences of 'Allvbride'.

DETAILED BOTANICAL DESCRIPTION

Plants used for the aforementioned photographs and following description were grown during the early summer in an outdoor nursery in Rijswijk, The Netherlands and under cultural practices typical of commercial *Veronica* production. During the production of the plants, day temperatures ranged from 12° C. to 26° C. and night temperatures ranged from 4° C. to 16° C. Plants were 14 months old when the photographs and the description were taken. In the following description, color references are made to The Royal Horticultural Society Colour Chart, 2015 Edition, except where general terms of ordinary dictionary significance are used.

Botanical classification: *Veronica longifolia* 'Allvbride'.

Parentage:

- *Female, or seed, parent*.—Proprietary selection of *Veronica longifolia* identified as code number 1-2013-74-11, not patented.
- *Male, or pollen, parent*.—Unknown selection of *Veronica longifolia*, not patented.

Propagation:

- *Type cutting*.—Terminal cuttings.
- *Time to initiate roots, summer*.—About 10 to 14 days at temperatures ranging from 12° C. to 30° C.
- *Time to produce a rooted young plant, summer*.—About 24 to 32 days at temperatures ranging from 12° C. to 30° C.
- *Root description*.—Fine, fleshy; typically white in color, actual color of the roots is dependent on substrate composition, water quality, fertilizer type and formulation, substrate temperature and physiological age of roots.
- *Rooting habit*.—Freely branching; dense.

Plant description:

- *Plant type*.—Herbaceous perennial.
- *Plant and growth habit*.—Upright and somewhat outwardly spreading plant habit; moderately vigorous growth habit.
- *Plant height, soil level to top of foliar plane*.—About 24.1 cm.
- *Plant height, soil level to top of floral plane*.—About 27.3 cm.
- *Plant width*.—About 17.5 cm.
- *Lateral branch description*.—Branching habit: Freely branching habit with about four main stems each with about five lateral branches. Length: About 17 cm. Diameter: About 3 mm. Internode length: About 2.7 cm. Strength: Strong. Aspect: Main stems, mostly upright; lateral branches, about 45° from main stem. Texture and luster: Densely pubescent; matte. Color: Developing, close to 144B; fully developed, close to 138A to 138B.

Leaf description:

- *Arrangement*.—Opposite, simple.
- *Length*.—About 4.9 cm.
- *Width*.—About 2.6 cm.
- *Shape*.—Ovate.
- *Apex*.—Acute.
- *Base*.—Truncate.
- *Margin*.—Serrate; slightly undulate.
- *Texture and luster, upper surface*.—Moderately pubescent; moderately glossy.
- *Texture and luster, lower surface*.—Moderately pubescent; matte.
- *Venation pattern*.—Pinnate.
- *Color*.—Developing leaves, upper surface: Close to 144B to 144C. Developing leaves, lower surface: Close to 144C. Fully expanded leaves, upper surface: Close to between NN137A and 147A; venation, close to 146B. Fully expanded leaves, lower surface: Close to 147B; venation, close to 146A.
- *Petioles*.—Length: About 1.3 cm. Diameter: About 2 mm by 1.75 mm. Strength: Strong. Texture and luster, upper surface: Moderately pubescent; matte. Texture and luster, lower surface: Smooth, glabrous; moderately glossy. Color, upper surface: Close to 144C. Color, lower surface: Close to 146B.

Flower description:

- *Flower arrangement and shape*.—Single campanulate flowers arranged on dense terminal and axillary racemes; flowers face mostly outwardly.
- *Flowering habit*.—Freely flowering habit with about 200 flowers developing per inflorescence and more than 1,800 flowers developing per plant during the flowering season.
- *Fragrance*.—None detected.
- *Natural flowering season*.—Long flowering period; plants flower continuously from the spring until the autumn in The Netherlands.
- *Flower longevity*.—Individual flowers last about one week on the plant; flowers persistent.
- *Flower buds*.—Length: About 4 mm. Diameter: About 2 mm. Shape: Ovoid. Texture and luster: Smooth, glabrous; matte. Color: Close to between NN155D and 157D; developing calyx, close to 138A.
- *Inflorescence height*.—About 13.9 cm.
- *Inflorescence diameter*.—About 2 cm.
- *Flower diameter*.—About 7 mm.
- *Flower height*.—About 6 mm.
- *Petals*.—Quantity and arrangement: Five in a single whorl; petals fused about 27.5% of the petal length from the base. Length: About 5.5 mm. Width: About 2.25 mm. Shape: Oblong; moderately concave. Apex: Obtuse. Margin: Entire. Texture and luster, upper surface: Distally, smooth, glabrous and proximally, densely pubescent; matte. Texture and luster, lower surface: Smooth, glabrous; slightly glossy. Color: When opening, upper and lower surfaces: Close to NN155D. Fully opened, upper and lower surfaces: Close to NN155D; color does not change with development.
- *Sepals*.—Quantity and arrangement: Four arranged in a single whorl. Length: About 1 mm to 1.75 mm. Width: About 0.5 mm. Shape: Ovate. Apex: Acute. Base: Broadly cuneate. Margin: Entire. Texture and luster, upper and lower surfaces: Smooth, glabrous; matte. Color: When opening and fully opened, upper surface: Close to 137B. When opening and fully opened, lower surface: Close to 138B.

*Peduncles*.—Length, terminal peduncle: About 13.7 cm. Length, axillary peduncle: About 7.1 cm. Diameter, terminal and axillary peduncles: About 2 mm. Aspect: Mostly upright. Strength: Strong. Texture and luster: Densely pubescent; matte. Color: Close to 138A to 138B.

*Pedicels*.—Length: About 0.8 mm. Diameter: About 0.3 mm. Aspect: About 45° from peduncle axis. Strength: Moderately strong. Texture and luster: Smooth, glabrous; slightly glossy. Color: Close to 138B.

*Reproductive organs*.—Stamens: Stamen development has not been observed on plants of the new *Veronica* to date. Pistils: Quantity per flower: One. Pistil length: About 6 mm. Stigma diameter: About 0.5 mm. Stigma shape: Club-shaped. Stigma color: Close to 145C to 145D. Style length: About 5.5 mm. Style color: Close to 157D. Ovary color: Close to 144B.

*Seeds and fruits*.—Seed and fruit development has not been observed on plants of the new *Veronica* to date.

Disease & pest resistance: Plants of the new *Veronica* have not been noted to be resistant to pathogens and pests common to *Veronica* plants to date.

Garden performance: Plants of the new *Veronica* have exhibited good garden performance and to be tolerant to rain, wind, high temperatures about 35° C. and to be suitable for USDA Hardiness Zones 4 through 9.

It is claimed:

1. A new and distinct *Veronica* plant named 'Allvbride' as illustrated and described.

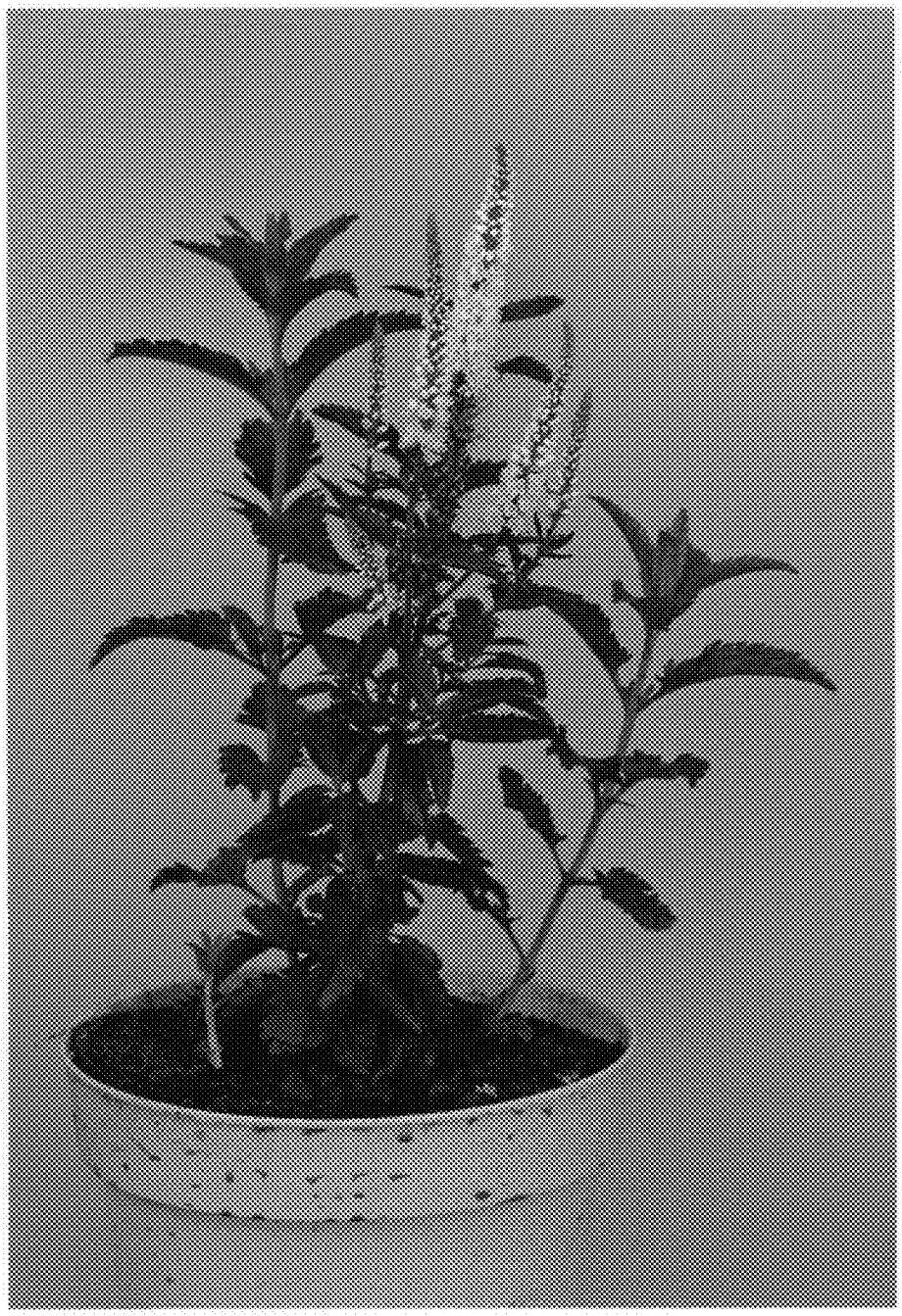

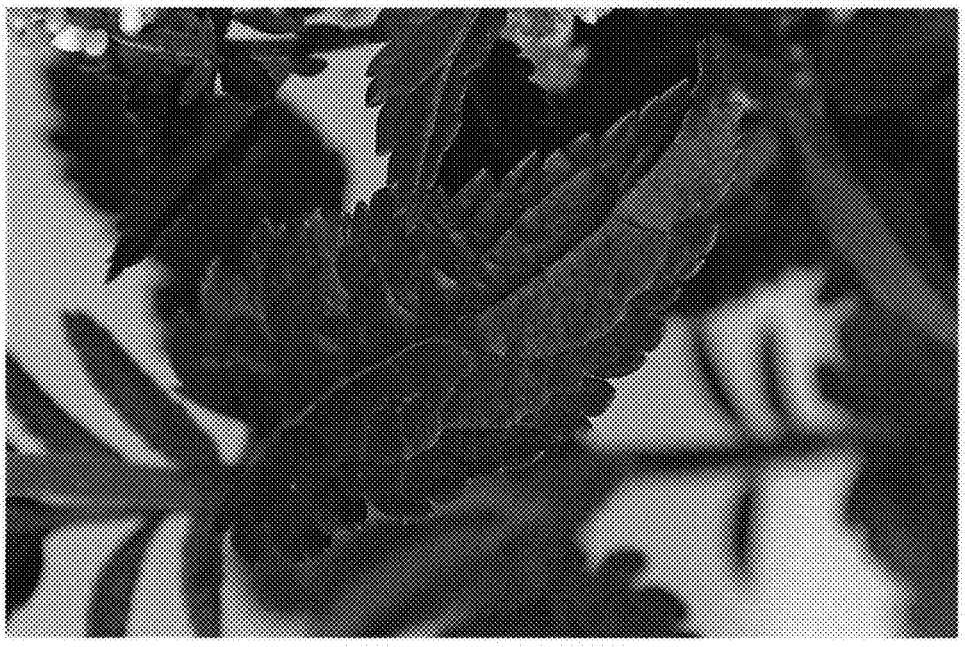
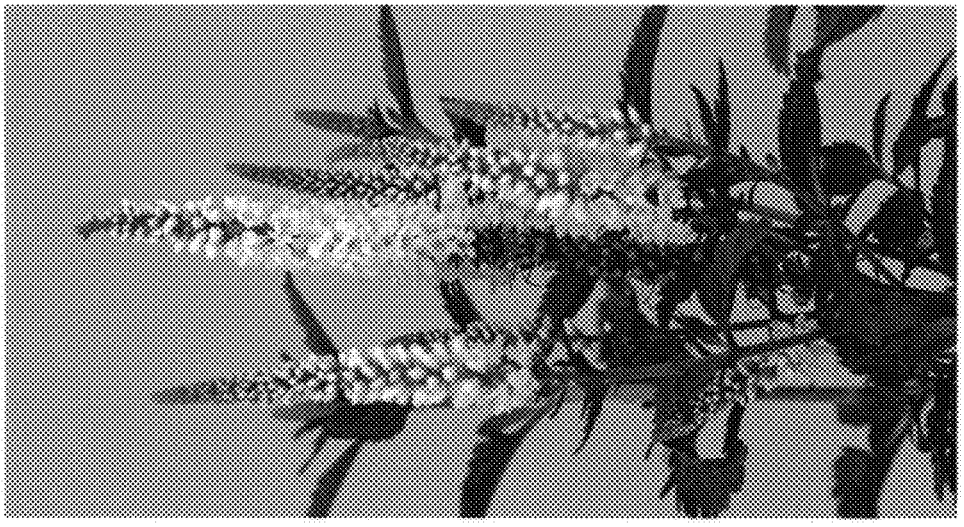

* * * * *